US011219353B2

(12) United States Patent
Elbaz et al.

(10) Patent No.: US 11,219,353 B2
(45) Date of Patent: Jan. 11, 2022

(54) SINGLE USE LARYNGOSCOPE HANDLE FOR USE IN DUAL COMPONENT LARYNGOSCOPE ASSEMBLY

(71) Applicant: TRUPHATEK INTERNATIONAL LTD., Netanya (IL)

(72) Inventors: Aviram Elbaz, Ein Sarid (IL); Igor Kobets, Pardess Hanna (IL); Gabriel Dan, Tel Aviv (IL)

(73) Assignee: TRUPHATEK INTERNATIONAL LTD., Netanya (IL)

( * ) Notice: Subject to any disclaimer, the term of this patent is extended or adjusted under 35 U.S.C. 154(b) by 378 days.

(21) Appl. No.: 16/287,904

(22) Filed: Feb. 27, 2019

(65) Prior Publication Data
US 2019/0191971 A1 Jun. 27, 2019

Related U.S. Application Data

(63) Continuation of application No. 14/417,498, filed as application No. PCT/IL2014/050745 on Aug. 20, 2014, now Pat. No. 10,244,922.
(Continued)

(51) Int. Cl.
*A61B 1/267* (2006.01)
*A61B 1/06* (2006.01)
(Continued)

(52) U.S. Cl.
CPC ...... *A61B 1/00105* (2013.01); *A61B 1/00032* (2013.01); *A61B 1/00062* (2013.01);
(Continued)

(58) Field of Classification Search
CPC ....... A61B 1/00103; A61B 1/267; A61B 1/06; A61B 1/00032; A61B 1/00062; A61B 1/00066; A61B 1/00137; A61B 1/00105
(Continued)

(56) References Cited

U.S. PATENT DOCUMENTS 330,139 A 11/1885 Meyer
744,271 A 11/1903 Adams
(Continued)

FOREIGN PATENT DOCUMENTS

DE 2621232 A1 11/1977
DE 20218560 U1 5/2003
(Continued)

OTHER PUBLICATIONS

Hilbro brochure, Green System Fiber Optic Laryngoscope, Interchangeable Light Guide Insert, Oct. 2001. [cited in U.S. Appl. No. 14/417,498].
(Continued)

*Primary Examiner* — Jessica Weiss
(74) *Attorney, Agent, or Firm* — BakerHostetler

(57) ABSTRACT

Single use laryngoscope handle for use in an ISO 7376 compatible dual component laryngoscope assembly with an illumination arrangement. The laryngoscope handle includes a plastic hand grip, a plastic end cap, and at least one plastic frangible member for engaging a hand grip and an end cap in a pre-actuated position of an end cap which is broken on application of a relatively minor manual detachment force to the end cap, thereby precluding subsequent use of the laryngoscope handle.

23 Claims, 5 Drawing Sheets

Related U.S. Application Data

(60) Provisional application No. 61/873,244, filed on Sep. 3, 2013.

(51) Int. Cl.
*A61B 1/00* (2006.01)
*H01M 2/10* (2006.01)
*H01M 50/213* (2021.01)

(52) U.S. Cl.
CPC ...... *A61B 1/00066* (2013.01); *A61B 1/00103* (2013.01); *A61B 1/00137* (2013.01); *A61B 1/06* (2013.01); *A61B 1/267* (2013.01); *H01M 50/213* (2021.01)

(58) Field of Classification Search
USPC .......... 600/185–199; 81/489, 177.1; 433/23; 362/109, 118, 157, 194
See application file for complete search history.

(56) References Cited

U.S. PATENT DOCUMENTS

| | | | |
|---|---|---|---|
| 846,495 A | 3/1907 | Morley | |
| 967,889 A | 8/1910 | Dethlefs et al. | |
| 1,785,343 A | 12/1930 | Gilbert | |
| 2,433,705 A | 12/1947 | Palmeter | |
| 3,426,749 A | 2/1969 | Jephcott | |
| 3,507,272 A | 4/1970 | Laerdal | |
| 3,598,113 A | 8/1971 | Moore | |
| 3,638,644 A | 2/1972 | Reick | |
| 3,766,909 A | 10/1973 | Ozbey | |
| 3,779,655 A | 12/1973 | Toyota | |
| 3,826,248 A * | 7/1974 | Gobels | A61B 1/00105 600/193 |
| 3,856,001 A | 12/1974 | Phillips | |
| 4,037,588 A | 7/1977 | Heckele | |
| 4,124,939 A | 11/1978 | Onoue | |
| 4,273,112 A | 6/1981 | Heine et al. | |
| 4,406,280 A | 9/1983 | Upsher | |
| 4,425,709 A | 1/1984 | Quenzi | |
| 4,437,458 A | 3/1984 | Upsher | |
| 4,488,655 A | 12/1984 | Itsubo et al. | |
| 4,519,514 A | 5/1985 | Agbay et al. | |
| 4,527,553 A | 7/1985 | Upsher | |
| 4,556,052 A | 12/1985 | Muller | |
| 4,557,256 A | 12/1985 | Bauman | |
| 4,565,187 A | 1/1986 | Soloway | |
| 4,570,614 A | 2/1986 | Bauman | |
| 4,579,108 A | 4/1986 | Bauman | |
| 4,583,527 A | 4/1986 | Musicant et al. | |
| 4,596,239 A | 6/1986 | Bauman | |
| 4,679,547 A | 7/1987 | Bauman | |
| 4,694,822 A | 9/1987 | Bauman | |
| 4,694,969 A | 9/1987 | Granat | |
| 4,862,772 A * | 9/1989 | Piperato | A61M 37/0076 81/9.22 |
| 4,878,486 A | 11/1989 | Slater | |
| 4,884,558 A | 12/1989 | Gorski et al. | |
| 4,930,495 A | 6/1990 | Upsher | |
| 4,958,624 A | 9/1990 | Stone et al. | |
| 4,972,825 A | 11/1990 | Vescovo, Jr. | |
| 5,038,766 A | 8/1991 | Parker | |
| 5,060,633 A | 10/1991 | Gibson | |
| 5,065,738 A | 11/1991 | Van Dam | |
| 5,095,624 A | 3/1992 | Ennis | |
| 5,169,257 A | 12/1992 | Liou | |
| 5,178,131 A | 1/1993 | Upsher | |
| D337,384 S | 7/1993 | Schucman | |
| 5,305,932 A * | 4/1994 | Iseli | B65D 47/242 222/521 |
| 5,355,870 A | 10/1994 | Lacy | |
| 5,501,651 A | 3/1996 | Bauman | |
| 5,529,570 A * | 6/1996 | Storz | A61B 1/07 600/185 |
| 5,651,760 A | 7/1997 | Upsher | |
| 5,678,718 A | 10/1997 | Morris et al. | |
| 5,685,079 A | 11/1997 | Brothers et al. | |
| 5,702,351 A | 12/1997 | Bar-Or et al. | |
| 5,727,682 A | 3/1998 | Abidin et al. | |
| 5,769,094 A | 6/1998 | Jenkins, Jr. et al. | |
| 5,873,818 A | 2/1999 | Rothfels | |
| 5,879,304 A | 3/1999 | Shuchman et al. | |
| 6,013,026 A | 1/2000 | Krauter et al. | |
| 6,139,491 A | 10/2000 | Heine et al. | |
| 6,213,937 B1 | 4/2001 | Vivenzio | |
| 6,354,993 B1 | 3/2002 | Kaplan et al. | |
| 6,394,295 B2 | 5/2002 | Claude | |
| 6,719,688 B2 | 4/2004 | Pecherer et al. | |
| 6,735,825 B1 | 5/2004 | Berman et al. | |
| 6,918,184 B2 | 7/2005 | Glesser | |
| 6,964,637 B2 | 11/2005 | Dalle et al. | |
| 7,007,392 B2 | 3/2006 | Ping | |
| 7,039,975 B1 | 5/2006 | Liao | |
| 7,128,710 B1 | 10/2006 | Cranton et al. | |
| D541,937 S * | 5/2007 | Yee | D24/136 |
| 7,214,184 B2 | 5/2007 | McMorrow | |
| 7,338,440 B1 | 3/2008 | Smith | |
| 7,608,040 B1 | 10/2009 | Dunst | |
| 7,611,459 B2 | 11/2009 | Geist et al. | |
| 7,736,304 B2 | 6/2010 | Pecherer | |
| 7,771,350 B2 | 8/2010 | Geist et al. | |
| 7,824,331 B1 | 11/2010 | Granton et al. | |
| 7,878,973 B2 | 2/2011 | Yee et al. | |
| 7,909,759 B2 | 3/2011 | Pecherer | |
| 8,142,353 B2 | 3/2012 | Pecherer et al. | |
| 8,162,826 B2 | 4/2012 | Pecherer et al. | |
| 8,251,898 B2 | 8/2012 | Pecherer | |
| 8,512,234 B2 | 8/2013 | Grey et al. | |
| 8,628,879 B2 | 1/2014 | Pecherer et al. | |
| 2002/0082477 A1 | 6/2002 | Kim | |
| 2002/0082478 A1 | 6/2002 | McGrath | |
| 2002/0087050 A1 | 7/2002 | Rudischhauser et al. | |
| 2003/0018239 A1* | 1/2003 | Cartledge | A61B 1/267 600/195 |
| 2003/0092967 A1 | 5/2003 | Fourie et al. | |
| 2003/0120131 A1 | 6/2003 | Pecherer et al. | |
| 2004/0034281 A1 | 2/2004 | Cartledge et al. | |
| 2004/0122292 A1 | 6/2004 | Dey et al. | |
| 2004/0127770 A1 | 7/2004 | McGrath | |
| 2004/0129741 A1 | 7/2004 | Stoneberg et al. | |
| 2004/0215062 A1 | 10/2004 | Dalle et al. | |
| 2005/0043590 A1 | 2/2005 | Mazzei et al. | |
| 2005/0090712 A1 | 4/2005 | Cubb | |
| 2005/0234303 A1 | 10/2005 | McMorrow | |
| 2006/0100483 A1 | 5/2006 | Sundet et al. | |
| 2006/0189847 A1* | 8/2006 | Yee | A61B 1/0669 600/199 |
| 2007/0093693 A1 | 4/2007 | Geist et al. | |
| 2007/0129606 A1 | 6/2007 | Pecherer | |
| 2008/0096099 A1 | 4/2008 | Pecherer et al. | |
| 2008/0234549 A1* | 9/2008 | Geist | A61B 1/00101 600/194 |
| 2009/0065007 A1 | 3/2009 | Wilkinson et al. | |
| 2009/0112067 A1 | 4/2009 | Baker | |
| 2009/0209816 A1 | 8/2009 | Nielsen et al. | |
| 2009/0270684 A1 | 10/2009 | Nielsen et al. | |
| 2010/0022843 A1 | 1/2010 | Pecherer et al. | |
| 2010/0041953 A1* | 2/2010 | Pecherer | A61B 1/267 600/193 |
| 2010/0191062 A1 | 7/2010 | Kieffer | |
| 2010/0217085 A1 | 8/2010 | Williams et al. | |
| 2010/0258563 A1 | 10/2010 | Parrinello et al. | |
| 2010/0261968 A1 | 10/2010 | Nearman et al. | |
| 2011/0060190 A1 | 3/2011 | Pecherer | |
| 2013/0062305 A1* | 3/2013 | Dahl | B65D 41/3404 215/257 |
| 2016/0000305 A1 | 1/2016 | Elbaz et al. | |

FOREIGN PATENT DOCUMENTS

| | | |
|---|---|---|
| DE | 102011018688 A1 | 10/2012 |
| EP | 0184588 A1 | 6/1986 |

(56) References Cited

FOREIGN PATENT DOCUMENTS

| | | |
|---|---|---|
| EP | 0653180 A1 | 5/1995 |
| GB | 685741 A | 1/1953 |
| GB | 806467 A | 12/1958 |
| WO | 2006131770 A2 | 12/2006 |

OTHER PUBLICATIONS

Medizintechnik KaWe Germeny, Laryngoscopes, Megalight F.O. [cited in U.S. Appl. No. 14/417,498].
PCT/IL2014/050745 International Search Report dated Dec. 12, 2014. [cited in U.S. Appl. No. 14/417,498].

* cited by examiner

SINGLE USE LARYNGOSCOPE HANDLE FOR USE IN DUAL COMPONENT LARYNGOSCOPE ASSEMBLY

CROSS-REFERENCE TO RELATED APPLICATIONS

This application is a Continuation of U.S. patent application Ser. No. 14/417,498, filed Jan. 26, 2015, which is a National Stage Entry of International Patent Application No. PCT/IL2014/050745, filed Aug. 20, 2014, which claims the benefit of U.S. Provisional Patent Application No. 61/873,244, filed Sep. 3, 2013. The contents of each of these applications are incorporated by reference herein in their entirety.

FIELD OF THE INVENTION

The invention relates to laryngoscope assemblies in general and laryngoscope handles in particular.

BACKGROUND OF THE INVENTION

ISO 7376 standardizes dual component laryngoscope assemblies including a removable double snap fit engagement of a laryngoscope blade into an operative intubation position on a laryngoscope handle. Dual component laryngoscope assemblies preferably include an illumination arrangement for facilitating an intubation. ISO compatible dual component laryngoscope assemblies can be classified into two types as follows:

First, a more recent so-called green type including a laryngoscope handle having a power source, an illumination source and a switching arrangement for selectively powering the illumination source in an operative intubation position of a laryngoscope blade. And second, a conventional type including a laryngoscope handle with a power source and a laryngoscope blade with an illumination source powered by the power source in an operative intubation position of the laryngoscope blade on the laryngoscope handle.

Such laryngoscope handles typically have sturdy metal constructions designed for sterilization between uses. However, sterilization is regarded as a relatively complicated, costly and time consuming procedure. Therefore there is a need for low cost laryngoscope handles designed to become inoperable after their intended single use.

SUMMARY OF THE INVENTION

The present invention is directed toward single use laryngoscope handles for use in ISO 7376 compatible dual component laryngoscope assemblies with an illumination arrangement. The single use laryngoscope handles include low cost plastic components including inter alia a plastic hand grip and a plastic end cap. The single use laryngoscope handles of the present invention are designed to satisfy two opposing use requirements as follows. On the one hand, an end cap is required to be sufficiently securely mounted on a hand grip to support the weight of a power source assembly in an upright handle position of a laryngoscope handle. And on the other hand, an end cap is required to be detached from a hand grip by application of a relatively minor manual detachment force which can be readily applied by a clinical user without the need for a separate tool to assist him such that an end cap cannot be re-attached onto a hand grip in a secure manner to satisfy the first requirement, thereby ensuring the laryngoscope handle is a single use medical device.

To satisfy these two opposing use requirements, the laryngoscope handles of the present invention include at least one plastic frangible member for engaging a hand grip and an end cap in a pre-actuated position of an end cap which is broken on application of a relatively minor manual detachment force to the end cap, thereby precluding subsequent use of the laryngoscope handle. Such actuation of an end cap leads to its detachment from a hand grip which in turn leads to a power source assembly contained in the hand grip to readily downwardly and outwardly slide therefrom by gravitational force in an upright handle orientation. Actuation of an end cap for detachment from a hand grip can be by way of a combined rotation of an end cap relative to a hand grip and a subsequent longitudinal directed force away from the hand grip. Alternatively, actuation can be by way of a longitudinal directed force only away from the hand grip. The single use laryngoscope handles of the present invention also afford that the plastic hand grip and end cap components can be readily separated from power source assemblies for recycling purposes, and the like.

Single use laryngoscope handles in accordance with the present invention can be designed for use in hitherto described green type laryngoscope assemblies including either single use or multiple use laryngoscope blades. Exemplary single use laryngoscope blades are disclosed in inter alia commonly owned U.S. Pat. No. 7,736,304 to Pecherer entitled Metal Laryngoscope Blade, and the like.

Alternatively, single use laryngoscope handles in accordance with the present invention can be designed for use in hitherto described conventional laryngoscope assemblies including either single use or multiple use laryngoscope blades. Exemplary single use laryngoscope blades are disclosed in inter alia commonly owned U.S. Pat. No. 5,879,304 to Shuchman et al. entitled Single Use Laryngoscope Blade, commonly owned U.S. Pat. No. 8,142,353 to Pecherer et al. entitled Metal Laryngoscope Blade with Illumination Assembly, and the like. Exemplary multiple use laryngoscope blades are disclosed in inter alia commonly owned U.S. Pat. No. 6,719,888 to Pecherer et al. entitled Light Guide Mount For Use in a Laryngoscope, and the like.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF THE DRAWINGS

Figure 1:
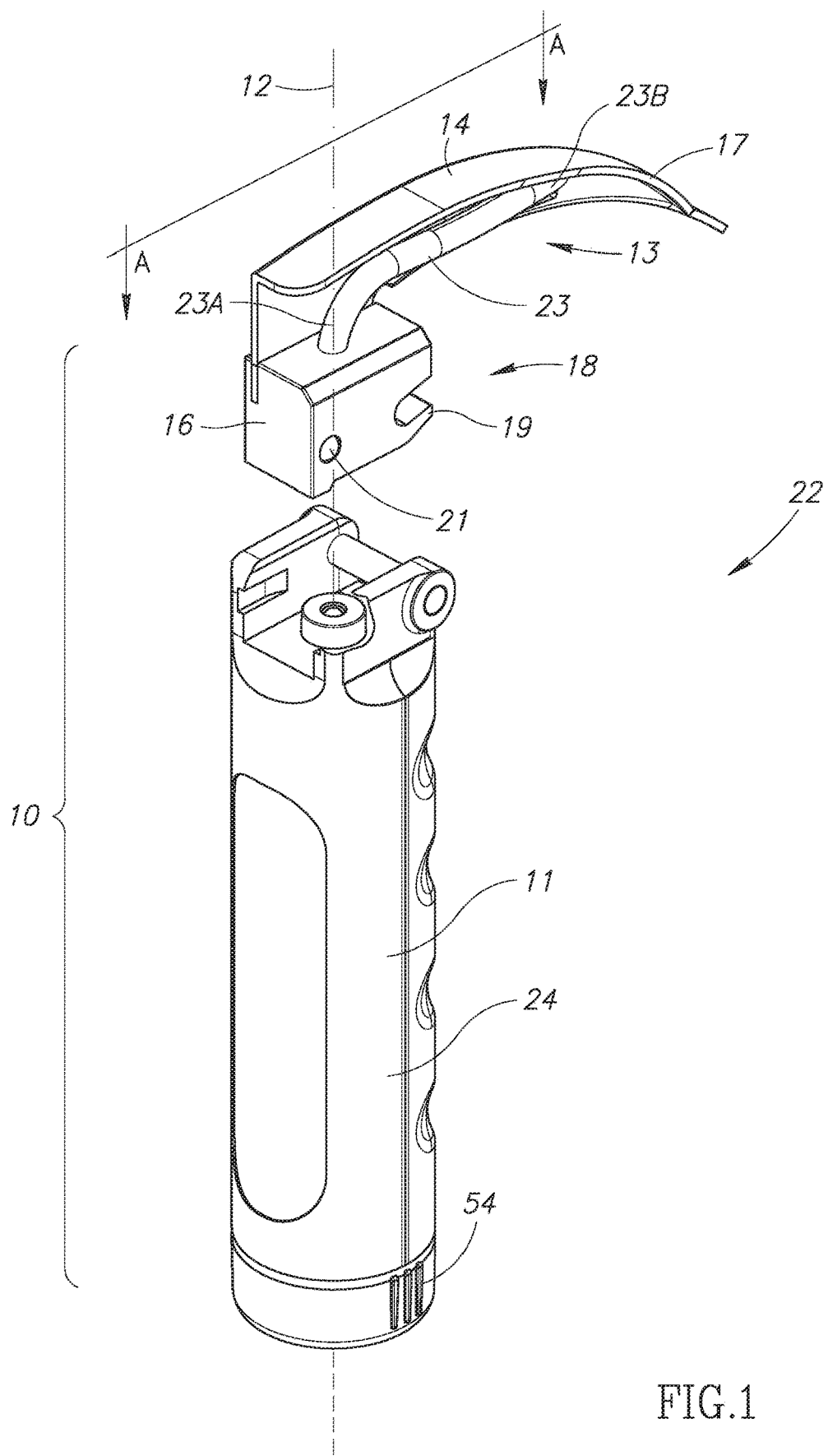
FIG. 1 is a front perspective view of a dissembled ISO 7376 so-called green laryngoscope assembly including a conventional laryngoscope blade and a preferred embodiment of a single use laryngoscope handle in accordance with the present invention.
Figure 2:
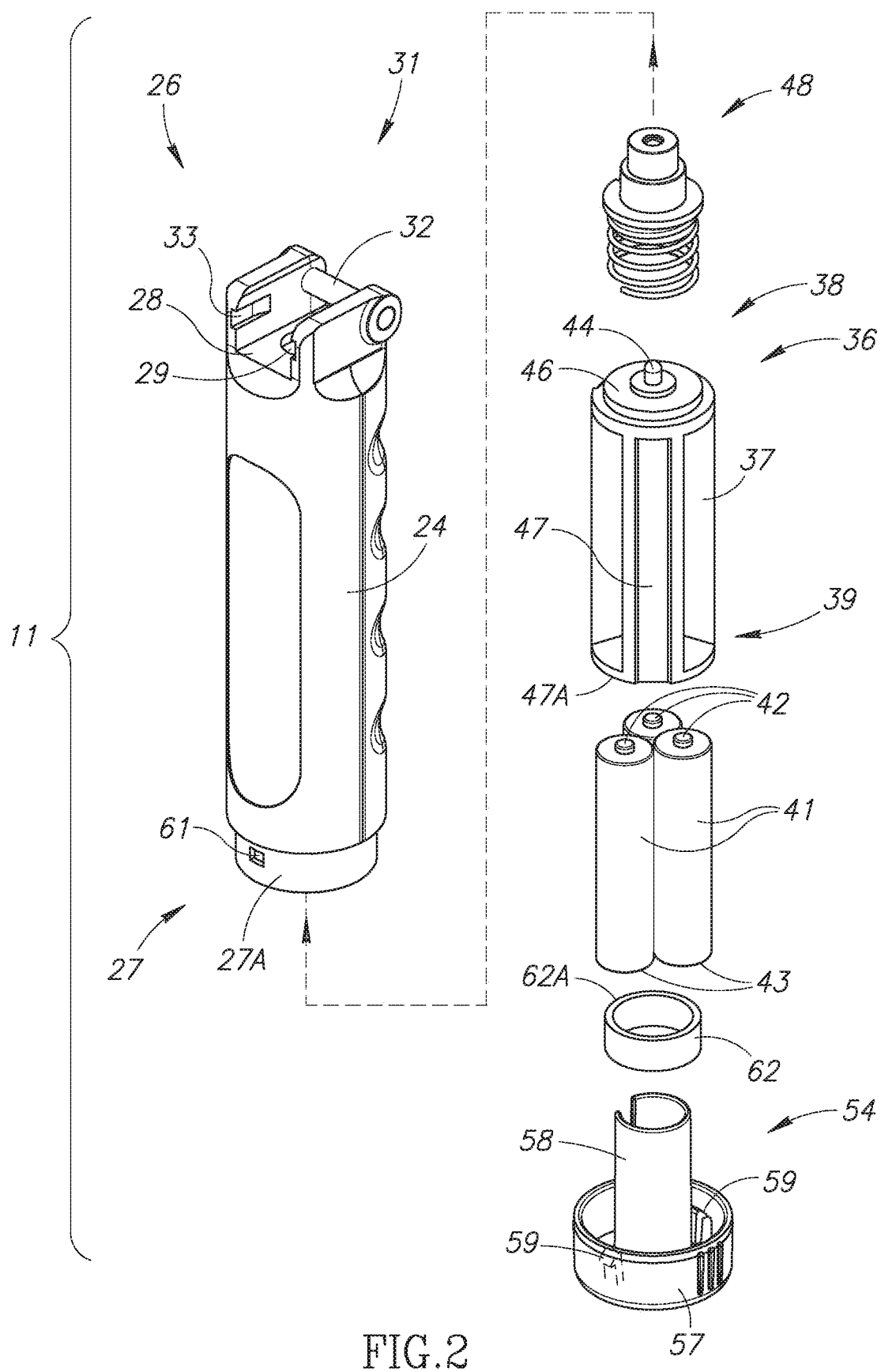
FIG. 2 is an exploded view of FIG. 1's laryngoscope handle.

FIGS. 1 and 2 show a dissembled ISO 7376 compatible laryngoscope assembly 10 including a single use laryngoscope handle 11 having a longitudinal handle axis 12 in an upright handle orientation. The laryngoscope assembly 10 includes a conventional metal or plastic laryngoscope blade 13 for a conventional dual snap fit engagement on the laryngoscope handle 11 into an operative intubation position generally transverse to the laryngoscope handle 11. The laryngoscope blade 13 can be intended for single use or designed for sterilization for multiple uses.

The laryngoscope blade 13 includes a spatula 14 with a proximal spatula end 16 and a distal spatula end 17 correspondingly adjacent to and remote from the laryngoscope handle 11 in its operative intubation position. The proximal spatula end 16 includes a standard blade hook arrangement 18 having a leading hook 19 and a pair of trailing outward directed spring loaded protrusions 21.

The laryngoscope assembly 10 includes an illumination arrangement 22 for providing illumination at the distal spatula end 17 in the operative intubation position. The illumination arrangement 22 includes a light guide 23 mounted on the laryngoscope blade 13 and extending from the proximal spatula end 16 to the distal spatula end 17 for conveying light from a proximal light guide end 23A to a distal light guide end 23B.

The laryngoscope handle 11 includes an elongated tubular plastic hand grip 24 having a leading hand grip end 26 and a trailing hand grip end 27. The leading hand grip end 26 is above the trailing hand grip end 27 in the upright handle orientation. The leading hand grip end 26 includes a transverse top wall 28 formed with a throughgoing aperture 29 along the longitudinal handle axis 12. The leading hand grip end 26 is formed with a standard handle hook arrangement 31 including a metal pin rod 32 on which the leading hook 19 is snap fitted thereon and a pair of opposite indents 33 remote from the metal pin rod 32 for snap fit receiving the pair of trailing outward directed spring loaded protrusions 21.

The laryngoscope handle 11 includes a power source assembly compartment 34 between the leading hand grip end 26 and the trailing hand grip end 27 for storing a power source assembly 36. The power source assembly 36 includes a plastic housing 37 having a leading housing end 38 and a trailing housing end 39. The plastic housing 37 stores three standard AAA batteries 41 with their positive terminals 42 towards the leading housing end 38 and their negative terminals 43 towards the trailing housing end 39. The leading housing end 38 is formed with a central terminal 44 in continuous electrical contact with the positive terminals 42. The leading housing end 38 is formed with an annular terminal 46 encircling the central terminal 44 and electrically isolated therefrom. The annular terminal 46 is in continuous electrical contact with the negative terminals 43 by an axial directed metal strip 47 extending from the annular terminal 46 to a metal plate 47A in electrical contact with the negative terminals 43.

The illumination arrangement 22 includes a LED housing 48 protruding through the throughgoing aperture 29 to be disposed above the transverse top wall 28 prior to double snap fit engagement of the laryngoscope blade 13 on the laryngoscope handle 11. The LED housing 48 includes a LED 49 with two LED terminals MA and MB. The LED terminal MA is in electrical contact with a central terminal cap 52 for selective electrical contact with the central terminal 44. The LED terminal 51B is in electrical contact with a metal spring 53 in continuous electrical contact with the annular terminal 46.

Figures 3, 4:
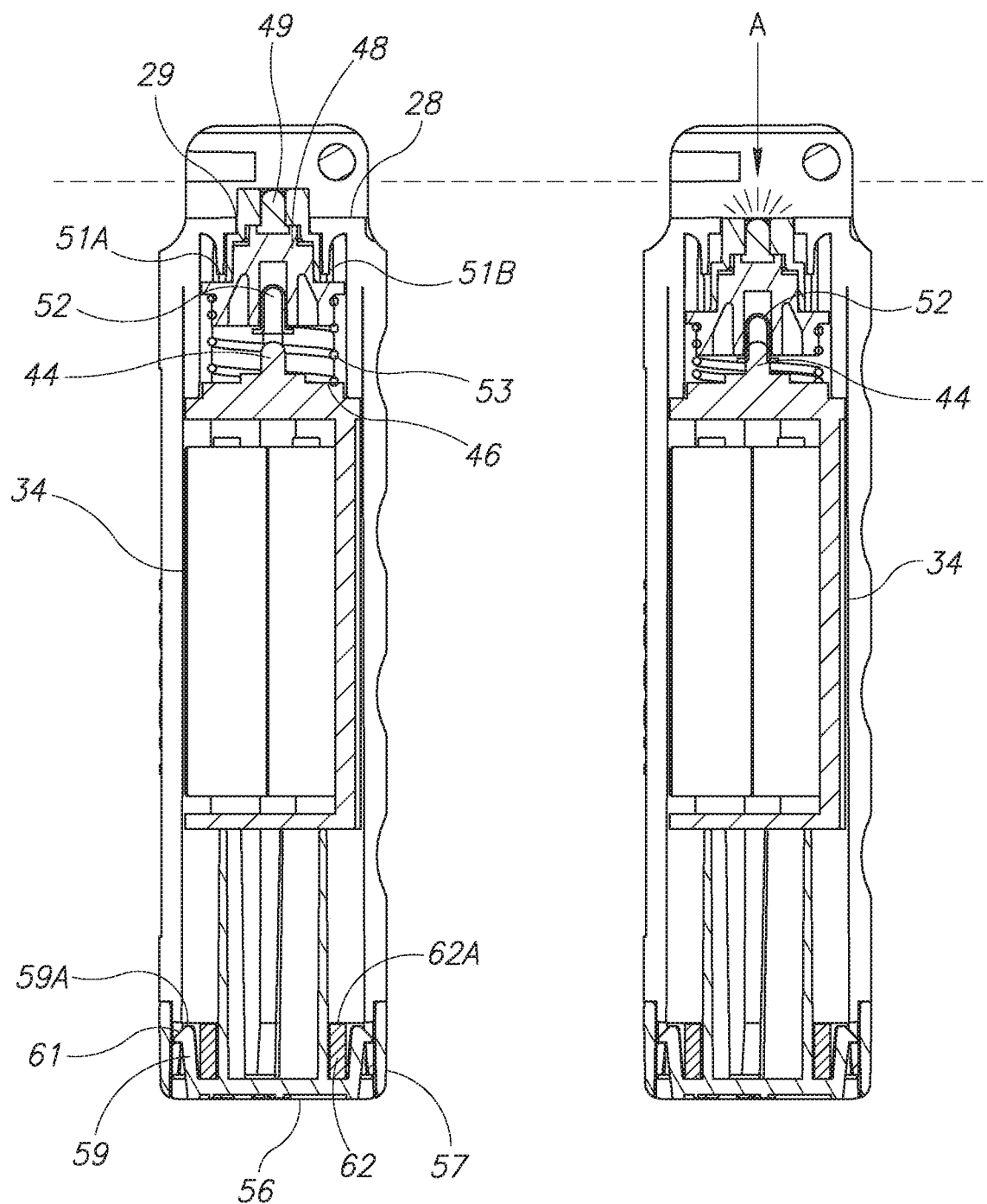
FIG. 3 is a longitudinal cross section of FIG. 1's laryngoscope handle along line A-A in FIG. 1 in a non-illuminating state.
FIG. 4 is a longitudinal cross section of FIG. 1's laryngoscope handle along line A-A in FIG. 1 in an illuminating state.

FIG. 3 shows the spring 53 biases the central terminal cap 52 away from the central terminal 44. FIG. 4 shows on double snap fit engagement of the laryngoscope blade 13 on the laryngoscope handle 11, the laryngoscope blade 11 imparts a downward force denoted by arrow A for overcoming the spring 53 such that the terminal cap 52 is in electrical contact with the central terminal 44 for operating the LED 49 for conveying light through the light guide 23 to the distal spatula end 17.

The laryngoscope handle 11 includes a plastic end cap 54 for interference fit mounting on the trailing hand grip end 27 in a pre-actuated position. The plastic end cap 54 includes a transverse end plate 56 and an upright end wall 57 for sliding mounting on a lowermost end 27A of the trailing hand grip end 27. The end plate 56 is formed with an axial directed central support member 58 for supporting the power source assembly 36 in the power source assembly compartment 34 at the leading hand grip end 26 in a pre-actuated position. The end plate 56 is also formed with a pair of opposite axial directed plastic frangible members 59 facing radial outward from the support member 58 for snug snap fit insertion into a pair of opposite throughgoing apertures 61 formed in the trailing hand grip end 27's lowermost end 27A such that the end cap 54 engages the trailing hand grip end 27. The frangible member pair 59 protrudes into the opposite throughgoing aperture pair 61 to abut against the upright end wall 57.

The end cap 54 includes a tubular cap ring 62 disposed between the upright support member 58 and the frangible member pair 59. The cap ring 62 is dimensioned heightwise such that its top surface 62A is substantially flush with the top surfaces 59A of the frangible member pair 59. The cap ring 62 traps the frangible member pair 59 in their intended throughgoing aperture pair 61 for their intentional snapping during actuation of the end cap 54 and not sliding out from the throughgoing apertures 61.

Figure 5:
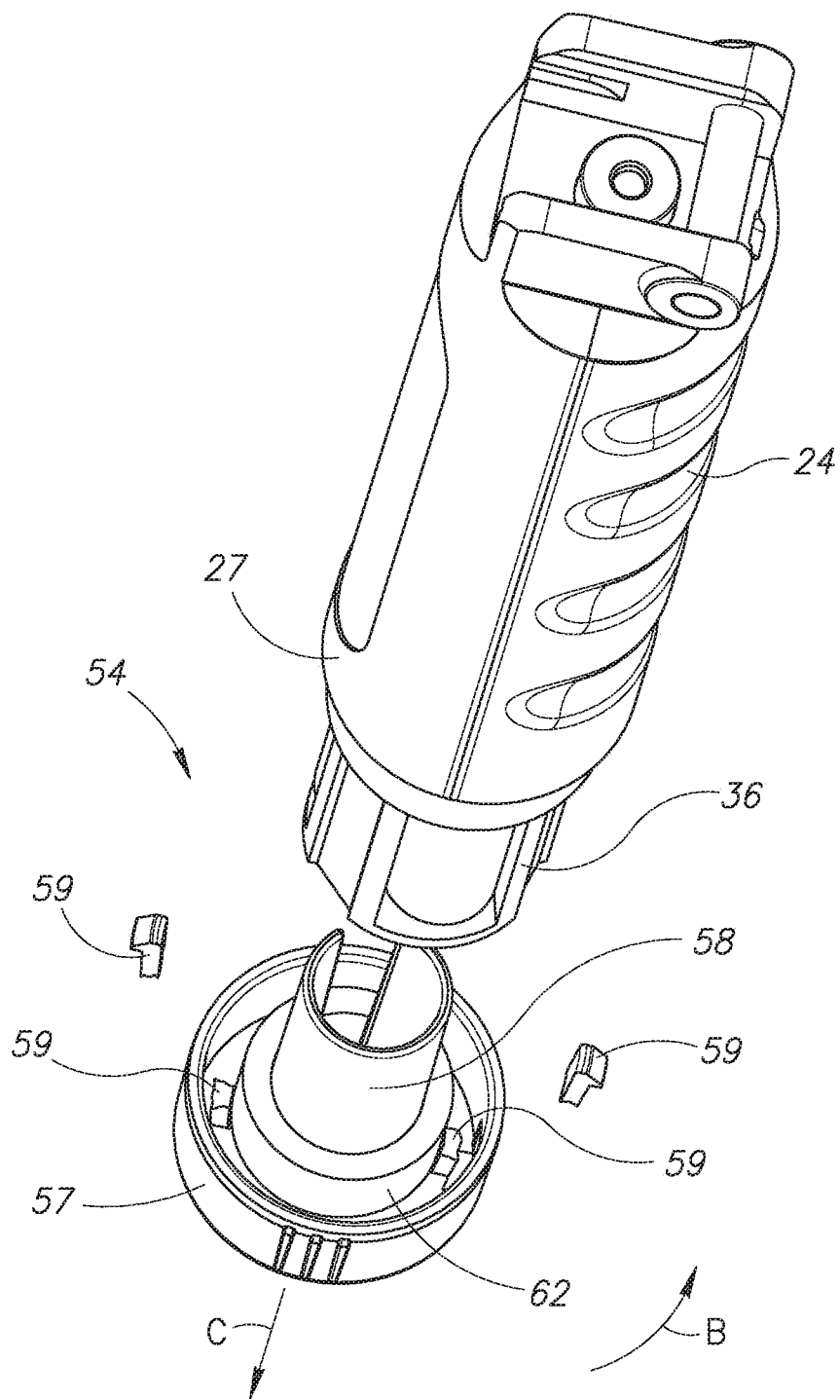
FIG. 5 is a front perspective view of FIG. 1's laryngoscope handle in an upright handle orientation after actuation.

FIG. 5 shows the manual actuation of the end cap 54 to preclude the laryngoscope handle 11 being re-used after an intended single use involves a combined user action of rotation denoted by arrow B to break the frangible member pair 59 and a subsequent longitudinal directed force denoted by arrow C to detach the end cap 54 from the trailing hand grip end 27. FIG. 5 also shows the frangible member pair 59 is snapped from the end plate 56 close to their junctures therewith. Consequently, the power source assembly 36 readily slides downwardly and outwardly from the trailing hand grip end 27 under gravitational force in the upright handle orientation. In the absence of the frangible member pair 59, re-attachment of the end cap 54 to the hand grip 24 will not provide a sufficient interference fitting to support the weight of the power source assembly 36 in the laryngoscope handle 11 in the upright handle orientation.

Figure 6:
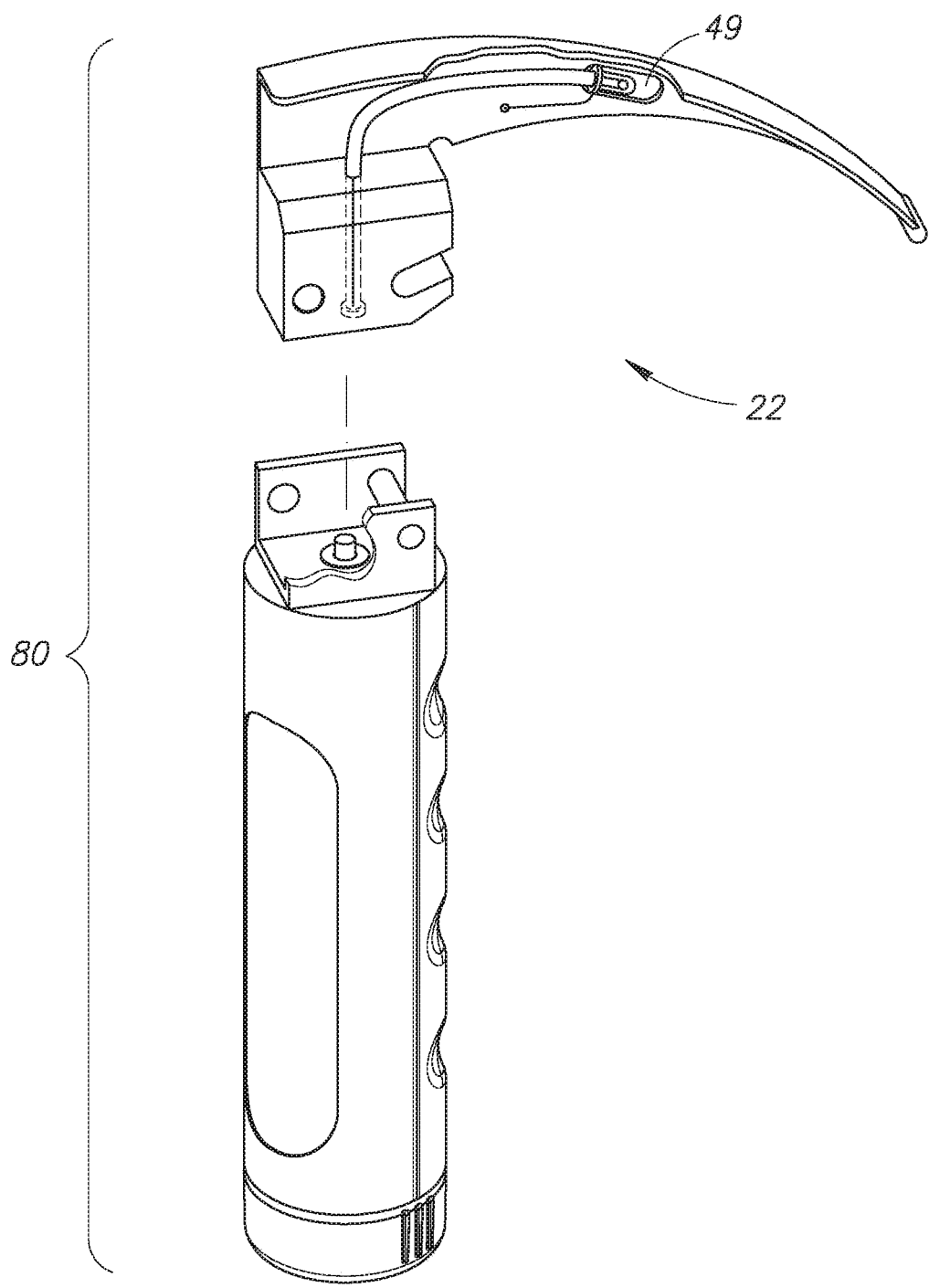
FIG. 6 is a front perspective view of a dissembled ISO 7376 conventional laryngoscope assembly including a conventional laryngoscope blade with an electrically operated illumination source and another preferred embodiment of a single use laryngoscope handle in accordance with the present invention.

FIG. 6 shows a dissembled conventional laryngoscope assembly 80 similar in construction and operation as the conventional laryngoscope assembly 10. The former 80 differs from the latter 10 insofar as the former 80 has an illumination arrangement 22 in which the LED 49 is disposed at the distal spatula end 17 and includes wires (not shown) for connecting the LED terminals 51A and 51B to the central terminal 44 and the annular terminal 46.

While the invention has been described with respect to a limited number of embodiments, it will be appreciated that many variations, modifications, and other applications of the invention can be made within the scope of the appended claims.

What is claimed is:

1. A single use laryngoscope handle comprising:
   a hand grip having a leading hand grip end and a trailing hand grip end, the leading hand grip end configured to releasably connect to a laryngoscope blade;
   a power source assembly compartment between the leading hand grip end and the trailing hand grip end, the power source assembly compartment configured to store a power source assembly;
   an end cap including an end plate and an upright end wall configured to slidingly mount on a lowermost end of the trailing hand grip end; and
   at least one frangible member extending from the end plate and configured for snap fit insertion into a respective aperture in the lowermost end of the trailing hand grip end such that the end cap engages the trailing hand grip end in a pre-actuated position;
   where the at least one frangible member is configured to protrude into the respective aperture and abut against the upright end wall in the pre-actuated position, where rotation of the end cap breaks the at least one frangible member such that the end cap disengages the trailing hand grip end in an actuated position, and where a subsequent longitudinally directed force detaches the end cap from the trailing hand grip end causing the power source assembly to slide out from the trailing hand grip end to preclude re-use of the laryngoscope handle.

2. The laryngoscope handle of claim 1, wherein the end cap is mounted on the trailing hand grip end in the pre-actuated position by an interference fit.

3. The laryngoscope handle of claim 1, wherein the at least one frangible member includes a portion facing radially outward for snap fit insertion into the respective aperture.

4. The laryngoscope handle of claim 1, further comprising a support member extending from the end plate for supporting the power source assembly in the power source assembly compartment at the leading hand grip end in the pre-actuated position.

5. The laryngoscope handle of claim 4, further comprising a cap ring between the support member and the at least one frangible member.

6. The laryngoscope handle of claim 5, wherein the cap ring is configured to trap the at least one frangible member in the respective aperture for snapping during actuation of the end cap and preventing the at least one frangible member from sliding out from the respective aperture.

7. The laryngoscope handle of claim 5, wherein a top surface of the cap ring is substantially flush with a top surface of the at least one frangible member.

8. The laryngoscope handle of claim 1, wherein the leading hand grip end comprises a handle hook arrangement including a pin rod configured to engage a leading hook of the laryngoscope blade.

9. The laryngoscope handle of claim 8, wherein the leading hand grip end further comprises a pair of opposite indents remote from the pin rod and configured to snap fit receive a pair of trailing outwardly directed spring loaded protrusions of the laryngoscope blade.

10. The laryngoscope handle of claim 9, wherein the leading hand grip end further includes a transverse top wall having a throughgoing aperture along a longitudinal handle axis.

11. The laryngoscope handle of claim 10, further comprising an illumination arrangement including a light source housing configured to protrude through the throughgoing aperture and be disposed above the transverse top wall prior to engagement of the laryngoscope blade on the laryngoscope handle.

12. A laryngoscope handle comprising:
    a hand grip having a leading hand grip end and a trailing hand grip end, the leading hand grip end configured to releasably connect to a laryngoscope blade, and where the leading hand grip end includes a transverse top wall having a throughgoing aperture;
    a power source assembly including a housing having a leading housing end and a trailing housing end;
    a power source assembly compartment between the leading hand grip end and the trailing hand grip end, the power source assembly compartment configured to receive the power source assembly;
    an end cap including an end plate and an upright end wall configured to slidingly mount on a lowermost end of the trailing hand grip end; and
    a connection member extending from the end plate and configured to engage the trailing hand grip end in a pre-actuated position, where rotation of the end cap disengages the connection member from the trailing hand grip end in an actuated position; and
    an illumination arrangement including an LED housing configured to protrude through the throughgoing aperture and be disposed above the transverse top wall when the laryngoscope blade is connected to the leading hand grip end.

13. The laryngoscope handle according to claim 12, wherein the connection member is configured for snap fit insertion into a respective aperture in the lowermost end of the trailing hand grip end in the pre-actuated position.

14. The laryngoscope handle according to claim 12, further comprising a support member extending from the end plate and configured to support the power source assembly in the power source assembly compartment at the leading hand grip end in the pre-actuated position.

15. The laryngoscope handle according to claim 12, wherein the leading housing end includes a central terminal and an annular terminal, the annular terminal electrically isolated from and encircling the central terminal.

16. The laryngoscope handle according to claim 15, wherein the trailing housing end includes a metal plate.

17. The laryngoscope handle according to claim 16, wherein the housing of the power source assembly further includes a metal strip extending from the annular terminal to the metal plate.

18. A single use laryngoscope handle comprising:
    a hand grip having a leading hand grip end and a trailing hand grip end, the leading hand grip end configured to releasably connect to a laryngoscope blade;
    a power source assembly compartment between the leading hand grip end and the trailing hand grip end, the power source assembly compartment configured to store a power source assembly;
    an end cap including an end plate and an upright end wall configured to slidingly mount on a lowermost end of the trailing hand grip end;
    at least one frangible member extending from the end plate and configured for snap fit insertion into a respective aperture in the lowermost end of the trailing hand grip end such that the end cap engages the trailing hand grip end in a pre-actuated position;

a support member extending from the end plate for supporting the power source assembly in the power source assembly compartment at the leading hand grip end in the pre-actuated position; and a cap ring between the support member and the at least one frangible member;

where rotation of the end cap breaks the at least one frangible member such that the end cap disengages the trailing hand grip end in an actuated position, and where a subsequent longitudinally directed force detaches the end cap from the trailing hand grip end causing the power source assembly to slide out from the trailing hand grip end to preclude re-use of the laryngoscope handle.

19. The laryngoscope handle of claim 18, wherein the cap ring is configured to trap the at least one frangible member in the respective aperture for snapping during actuation of the end cap and preventing the at least one frangible member from sliding out from the respective aperture.

20. A single use laryngoscope handle comprising:

a hand grip having a leading hand grip end and a trailing hand grip end, the leading hand grip end comprising a handle hook arrangement including a pin rod configured to engage a leading hook of the laryngoscope blade, a pair of opposite indents remote from the pin rod and configured to snap fit receive a pair of trailing outwardly directed spring loaded protrusions of the laryngoscope blade, and a transverse top wall having a throughgoing aperture along a longitudinal handle axis;

a power source assembly compartment between the leading hand grip end and the trailing hand grip end, the power source assembly compartment configured to store a power source assembly;

an end cap including an end plate and an upright end wall configured to slidingly mount on a lowermost end of the trailing hand grip end; and at least one frangible member extending from the end plate and configured for snap fit insertion into a respective aperture in the lowermost end of the trailing hand grip end such that the end cap engages the trailing hand grip end in a pre-actuated position;

where rotation of the end cap breaks the at least one frangible member such that the end cap disengages the trailing hand grip end in an actuated position, and where a subsequent longitudinally directed force detaches the end cap from the trailing hand grip end causing the power source assembly to slide out from the trailing hand grip end to preclude re-use of the laryngoscope handle.

21. The laryngoscope handle of claim 20, further comprising a support member extending from the end plate for supporting the power source assembly in the power source assembly compartment at the leading hand grip end in the pre-actuated position.

22. The laryngoscope handle of claim 21, further comprising a cap ring between the support member and the at least one frangible member, the cap ring configured to trap the at least one frangible member in the respective aperture for snapping during actuation of the end cap and preventing the at least one frangible member from sliding out from the respective aperture.

23. The laryngoscope handle of claim 20, further comprising an illumination arrangement including a light source housing configured to protrude through the throughgoing aperture and be disposed above the transverse top wall prior to engagement of the laryngoscope blade on the laryngoscope handle.

\* \* \* \* \*